(12) United States Patent
Graves et al.

(10) Patent No.: US 9,709,531 B1
(45) Date of Patent: Jul. 18, 2017

(54) SYSTEMS AND METHODS FOR ASSAYING A LIQUID SAMPLE OR ALUMINA COLUMN FOR MOLYBDENUM CONTENT

(71) Applicant: Mallinckrodt Nuclear Medicine LLC, Maryland Heights, MO (US)

(72) Inventors: Kevin Bartlett Graves, Catawissa, MO (US); Bryan Scott Petrofsky, St. Louis, MO (US); Sumit Verma, Chesterfield, MO (US)

(73) Assignee: Mallinckrodt Nuclear Medicine LLC, Maryland Heights, MO (US)

( * ) Notice: Subject to any disclaimer, the term of this patent is extended or adjusted under 35 U.S.C. 154(b) by 0 days.

(21) Appl. No.: 15/203,452

(22) Filed: Jul. 6, 2016

(51) Int. Cl.
 *H01J 47/00* (2006.01)
 *G01N 27/66* (2006.01)

(52) U.S. Cl.
 CPC .................. *G01N 27/66* (2013.01)

(58) Field of Classification Search
 CPC .............. G01T 1/185; G01T 3/008
 See application file for complete search history.

(56) References Cited

U.S. PATENT DOCUMENTS

| | | | |
|---|---|---|---|
| 2,445,305 A | 7/1948 | Hochgesang | |
| 2,358,632 A | 1/1951 | Tompkins | |
| 2,858,465 A | 10/1958 | Ludeman | |
| 3,119,036 A | 1/1964 | Braestrup et al. | |
| 3,366,790 A | 1/1968 | Zagorites et al. | |
| 3,843,884 A | 10/1974 | Evans | |
| 4,511,799 A | 4/1985 | Bjorkholm | |
| 5,095,217 A * | 3/1992 | Attix | H01J 47/024 250/374 |
| 5,908,884 A | 6/1999 | Kawamura et al. | |
| 2014/0264056 A1 | 9/2014 | Graves et al. | |

OTHER PUBLICATIONS

An Introduction to Ionization Chambers, Oak Ridge Associated Universities, Museum Directory, Jul. 31, 2009, pp. 2, http://www.orau.org/ptp/collection/ionchamber/introionizationchamberr.htm.
Prussin, S.G. et al., "An Instrumented Shield System for Calibration of Technetium-99m", Journal of Nuclear Medicine Technology, Society of Nuclear Medicine, Sep. 1, 1995, vol. 23, No. 3, pp. 202-208.
International Search Report and Written Opinion of the International Searching Authority regarding PCT/US2017/012788 mailed on Apr. 21, 2017, pp. 13.

* cited by examiner

*Primary Examiner* — Kiho Kim
(74) *Attorney, Agent, or Firm* — Armstrong Teasdale LLP

(57) ABSTRACT

A system for assaying a sample for Molybdenum-99 content includes an inner ionization chamber including a well configured to receive the sample, an outer ionization chamber concentric with the inner ionization chamber, attenuating material positioned in the well, and a computing device. The computing device is configured to determine a first Molybdenum-99 content value of the sample based on a first current measured in the inner ionization chamber, determine a second Molybdenum-99 content value of the sample based on a second current measured in the outer ionization chamber, and determine a final Molybdenum-99 content value based on the first and second Molybdenum-99 content values.

20 Claims, 3 Drawing Sheets

SYSTEMS AND METHODS FOR ASSAYING A LIQUID SAMPLE OR ALUMINA COLUMN FOR MOLYBDENUM CONTENT

FIELD

The field of the disclosure relates generally to detecting a radioactive content of a sample, and more particularly, to assaying a sample for Molybdenum.

BACKGROUND

Molybdenum-99 ($^{99}$Mo) is the parent radioisotope used for generating Technetium-99m ($^{99m}$Tc) for diagnostic medical purposes. Specifically, quantities up to 6000 Curies (Ci) can be used to produce Technetium generators. Accordingly, samples from the formulation process must be tested (i.e., assayed) for Molybdenum-99 content.

Conventional assaying methods require performing a first Molybdenum-99 assay using a first radiometric assay device, and subsequently transporting the sample to a different location to perform a separate, second Molybdenum-99 assay using a second radiometric assay device. Molybdenum-99 content in samples is typically too high to safely remove the sample from a hot cell to perform other measurements. When the sample is a filled alumina column, only hot cell assay systems may be used. Further, in conventional assaying methods, a technician measures a low activity sample using a radiometric assay device and manually calculates the assay value. Also, technicians transporting the sample are exposed to the sample during the process. Accordingly, known methods for assaying a sample for Molybdenum-99 are time-consuming, inefficient, less accurate, and expose the technician to a radioactive dose.

This Background section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

SUMMARY

In one aspect, a system for assaying a sample for Molybdenum-99 content includes an inner ionization chamber including a well configured to receive the sample, an outer ionization chamber concentric with the inner ionization chamber, attenuating material positioned in the well, and a computing device. The computing device is configured to determine a first Molybdenum-99 content value of the sample based on a first current measured in the inner ionization chamber, determine a second Molybdenum-99 content value of the sample based on a second current measured in the outer ionization chamber, and determine a final Molybdenum-99 content value based on the first and second Molybdenum-99 content values.

In another aspect, a method for assaying a sample for Molybdenum-99 content includes placing the sample in a well of an inner ionization chamber, wherein the well includes attenuating material, measuring a first current in the inner ionization chamber, and measuring a second current in an outer ionization chamber, wherein the outer ionization chamber is concentric with the inner ionization chamber. The method further includes determining, using a computing device, a first Molybdenum-99 content value of the sample from the first measured current, determining, using the computing device, a second Molybdenum-99 content value of the sample from the second measured current, and determining, using the computing device, a final Molybdenum-99 content value based on the first and second Molybdenum-99 content values.

In yet another aspect, a radiation detection device for assaying a sample for Molybdenum-99 content includes an inner ionization chamber including a well that receives the sample, wherein a first current is generated in the inner ionization chamber in response to an amount of Molybdenum-99 present in the sample, an outer ionization chamber concentric with the inner ionization chamber, wherein a second current is generated in the outer ionization chamber in response to the amount of Molybdenum-99 present in the sample, and attenuating material positioned in the well of the inner ionization chamber.

Various refinements exist of the features noted in relation to the above-mentioned aspects. Further features may also be incorporated in the above-mentioned aspects as well. These refinements and additional features may exist individually or in any combination. For instance, various features discussed below in relation to any of the illustrated embodiments may be incorporated into any of the above-described aspects, alone or in any combination.

BRIEF DESCRIPTION OF THE DRAWINGS

Corresponding reference characters indicate corresponding parts throughout the several views of the drawings.

DETAILED DESCRIPTION

Figure 1:
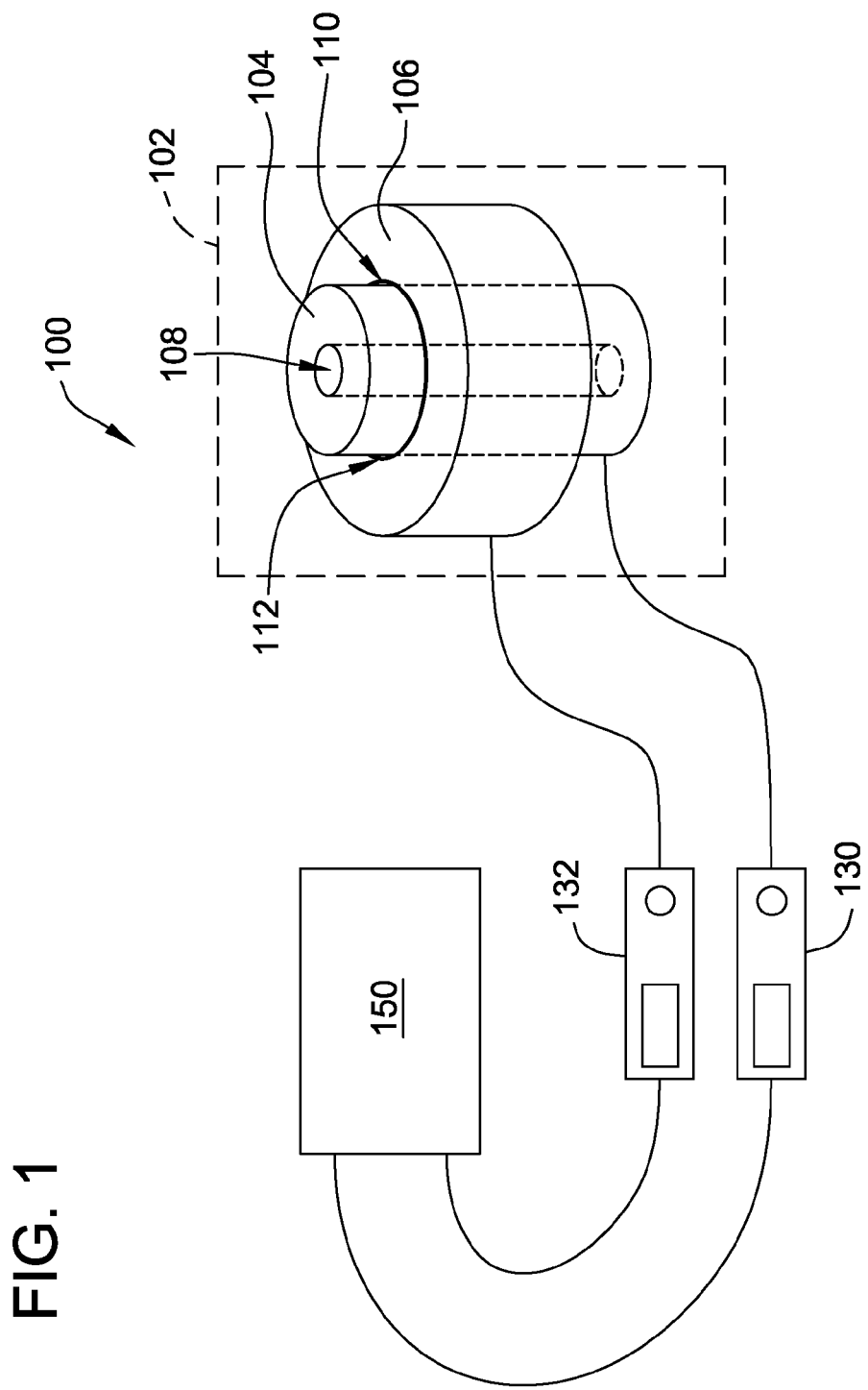
FIG. 1 is a schematic diagram of a system of one embodiment for assaying a sample.
Figure 2:
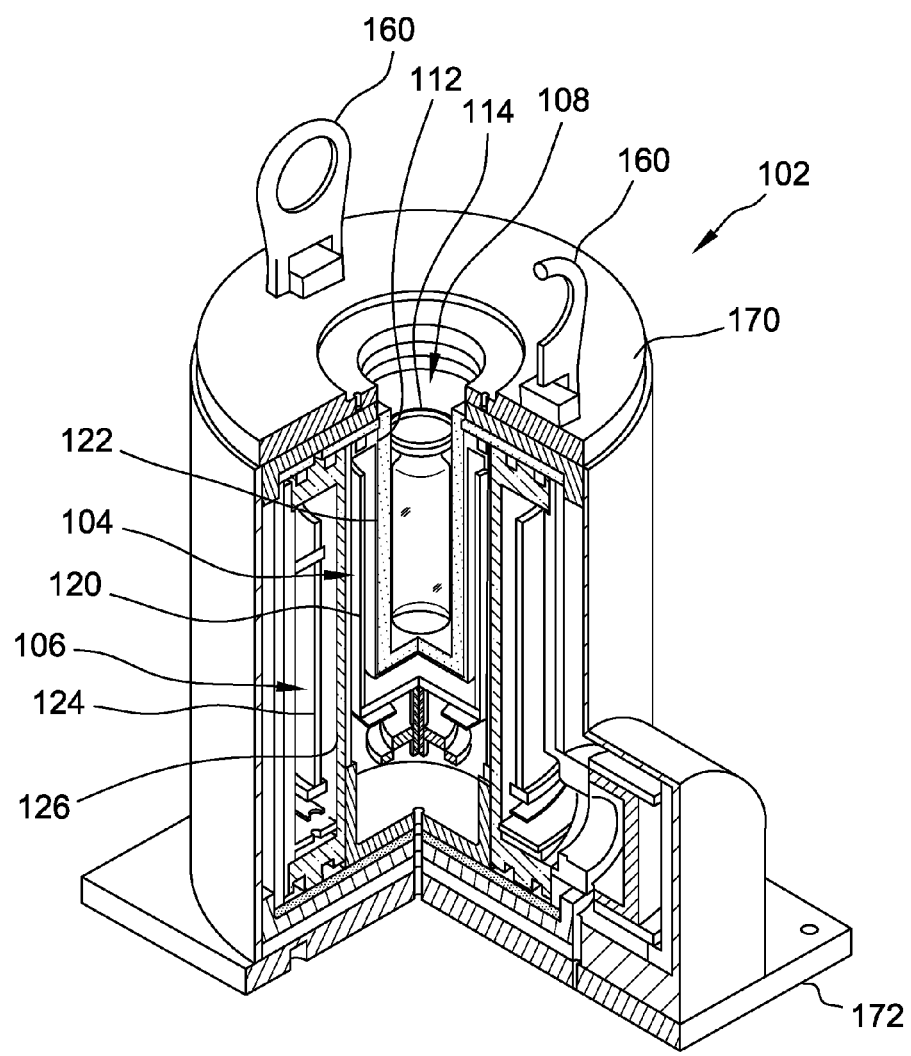
FIG. 2 is a perspective partial cut-away view of a radiation detection device that may be used with the system shown in FIG. 1.

Referring to FIG. 1, a system for assaying a sample is indicated generally at 100. The sample may include, for example, a liquid sample or an alumina column. FIG. 2 is a perspective partial cut-away view of a radiation detection device 102 that may be used with the system shown in FIG. 1. System 100 includes a radiation detection device 102 having a first, inner ionization chamber 104 and a second, outer ionization chamber 106. First and second ionization chambers 104 and 106 are both annular and are concentric with one another. Each of first and second ionization chambers 104 and 106 contains a gas to facilitate detecting a radioactive content of a sample, as described in more detail below.

First ionization chamber 104 includes a first well 108, and second ionization chamber includes a second well 110. Further, first and second ionization chambers 104 and 106 are concentric with one another, such that the first ionization chamber 104 is positioned within second well 110. An attenuating material 112 is positioned in first well 108 to filter out low energy gamma rays emitted from the sample and prevent those low energy gamma rays from reaching first and second ionization chambers 104 and 106. Attenuating material 112 may be, for example, lead or tungsten. In this embodiment, attenuating material 112 has a thickness of approximately 0.25 inches. Alternatively, attenuating material 112 may have any suitable dimensions for filtering out low energy gamma rays, as described herein.

To assay a sample, a vial 114 or other container storing the sample therein is inserted into first well 108. Vial 114 may be, for example, a 15 milliliter (ml) French Square vial including a 5 ml sample. In this embodiment, the sample includes a sample of Molybdenum-99 ($^{99}$Mo). The sample may be a liquid sample or an alumina column. First ionization chamber 104 facilitates detecting a first Molybdenum-99 content value of the sample, and second ionization chamber 106 facilitates detecting a second Molybdenum-99 content value of the sample. The content values are compared to verify they are generally in agreement with one another, and are combined (e.g., averaged) to generate a final Molybdenum-99 content value. Measuring the Molybdenum-99 content using two separate chambers and combining the values from each chamber facilitates ensuring an accurate determination of the Molybdenum-99 content. After assaying the sample, the sample may be disposed of using a radioactive waste system (not shown).

More specifically, first and second ionization chambers 104 and 106 each contain a gas, a positive electrode, and a negative electrode. First ionization chamber 104 includes an outer electrode 120 and an inner electrode 122, and second ionization chamber 106 includes an outer electrode 124 and an inner electrode 126. Within each of first and second ionization chambers 104, one electrode operates as the positive electrode and one electrode operates as the negative electrode. Specifically, in each of first and second ionization chambers 104 and 106, a voltage is applied between the positive and negative electrodes to create an electric field in the gas. For example, relative to the negative electrode, a voltage of several hundred volts may be applied to the positive electrode. The voltage difference between the positive and negative electrodes in first and second ionization chambers 104 and 106 may be applied using any suitable internal or external power source. Radiation emitted from the sample ionizes the gas, and the generated ions move in response to the electric field, consequently generating a current in the respective ionization chamber. The amount of radiation corresponds to the amount of ionization, and accordingly, the amount of current. Accordingly, by detecting a first current in first ionization chamber 104 and a second current in second ionization chamber 106, the radioactive content of the sample can be determined.

As described above, attenuating material 112 is positioned in first well 108 to filter out low energy gamma rays emitted from the sample and prevent those low energy gamma rays from reaching first and second ionization chambers 104 and 106. Accordingly, the majority of any gamma rays (i.e., 142.63 kiloelectron volts (keV) emissions and 140.51 keV emissions) emitted do not reach first and second ionization chambers 104 and 106, but are blocked by attenuating material 112.

In this embodiment, first ionization chamber 104 is a high-pressure Xenon gas chamber that includes Xenon gas. Using Xenon gas in first ionization chamber 104 facilitates increased sensitivity to radiation emitted from the Molybdenum-99 in the sample. With vial 114 positioned in first well 108, radiation from the Molybdenum-99 in the sample ionizes the gas in first ionization chamber 104, generating the first current in first ionization chamber 104. A first current measurement device 130 electrically connected to first ionization chamber 104 measures the first current. In this embodiment, first current measurement device 130 is a source measurement unit (SMU). The SMU may be, for example, a Keithley® Picoammeter (Keithley is a registered trademark of Keithley Instruments, Inc., Cleveland, Ohio). Alternatively, first current measurement device 130 may be any device capable of measuring the first current in first ionization chamber 104.

Second ionization chamber 106 is also a high-pressure Xenon gas chamber in this embodiment. Using Xenon gas in second ionization chamber 106 facilitates increased sensitivity to radiation emitted from the Molybdenum-99 in the sample. Accordingly, with vial 114 positioned in first well 108, radiation from the Molybdenum-99 in the sample also ionizes the gas in second ionization chamber 106, generating the second current in second ionization chamber 106.

A gas pressure in each of first and second ionization chambers 104 and 106 is set during a calibration process. In this embodiment, a specific gas pressure is determined for each chamber 104 and 106 based on a diameter and active volume of the respective chamber. Further, during the calibration process, the gas pressures in each chamber 104 and 106 may be adjusted experimentally until measured assay values for both chambers 104 and 106 are in agreement.

A second current measurement device 132 electrically connected to second ionization chamber 106 measures the second current. In this embodiment, second current measurement device 132 is a source measurement unit (SMU). The SMU may be, for example, a Keithley® Picoammeter (Keithley is a registered trademark of Keithley Instruments, Inc., Cleveland, Ohio). Alternatively, second current measurement device 132 may be any device capable of measuring the second current in second ionization chamber 106.

In this embodiment, a computing device 150 is communicatively coupled to first and second current measurement devices 130 and 132. Computing device 150 receives the first current measurement and the second current measurement from first and second current measurement devices 130 and 132, respectively.

Radiation detection device 102 includes a pair of lifting eyes 160 in this embodiment. As radiation detection device 102 may be relatively heavy (e.g., greater than 60 lbs), lifting eyes 160 aid in lifting and transporting radiation detection device 102. Radiation detection device 102 also includes an aluminum top 170 and an aluminum bottom 172. Alternatively, top and bottom 170 and 172 may be made of any suitable structural material (e.g., tungsten, etc.).

Figure 3:
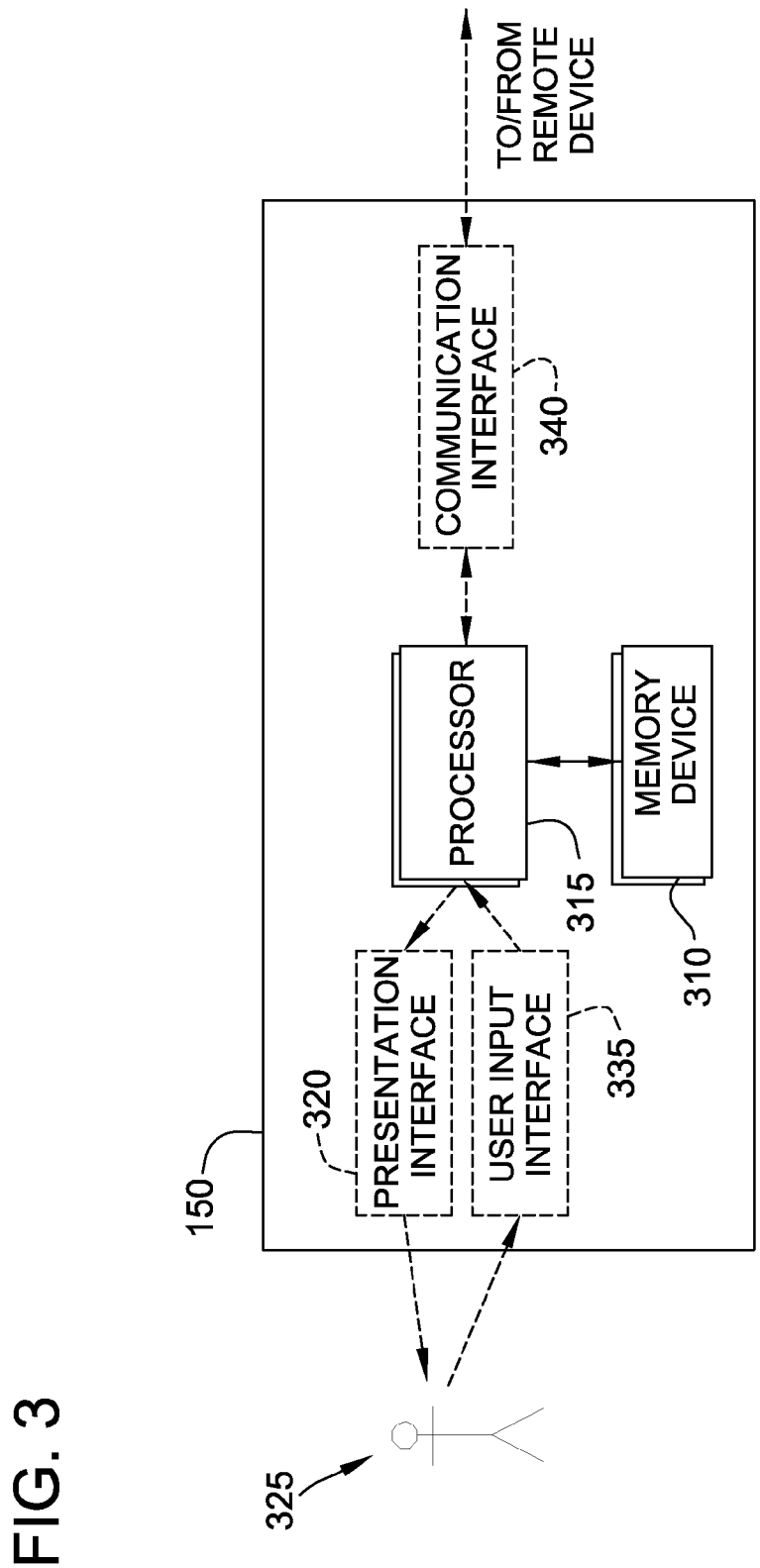
FIG. 3 is a block diagram of a computing device that may be used with the system shown in FIG. 1.

FIG. 3 is a block diagram of computing device 150. Computing device 150 includes at least one memory device 310 and a processor 315 that is coupled to memory device 310 for executing instructions. In this embodiment, executable instructions are stored in memory device 310, and computing device 150 performs one or more operations described herein by programming processor 315. For example, processor 315 may be programmed by encoding an operation as one or more executable instructions and by providing the executable instructions in memory device 310.

Processor 315 may include one or more processing units (e.g., in a multi-core configuration). Further, processor 315 may be implemented using one or more heterogeneous processor systems in which a main processor is present with secondary processors on a single chip. As another illustrative example, processor 315 may be a symmetric multi-processor system containing multiple processors of the same type. Further, processor 315 may be implemented using any suitable programmable circuit including one or more systems and microcontrollers, microprocessors, programmable logic controllers (PLCs), reduced instruction set circuits (RISC), application specific integrated circuits (ASIC), programmable logic circuits, field programmable gate arrays (FPGA), and any other circuit capable of executing the functions described herein. In this embodiment, processor 315 determines the Molybdenum-99 content of the sample from the first and second current measurements, as described herein. Processor 315 may also control operation of first and second current measurement devices 130 and 132.

Memory device 310 is one or more devices that enable information such as executable instructions and/or other data to be stored and retrieved. Memory device 310 may include one or more computer readable media, such as, without limitation, dynamic random access memory (DRAM), static random access memory (SRAM), a solid state disk, and/or a hard disk. Memory device 310 may be configured to store, without limitation, application source code, application object code, source code portions of interest, object code portions of interest, configuration data, execution events and/or any other type of data.

In this embodiment, computing device 150 includes a presentation interface 320 that is coupled to processor 315. Presentation interface 320 presents information, such as application source code and/or execution events, to a user 325, such as a technician. For example, presentation interface 320 may include a display adapter (not shown) that may be coupled to a display device, such as a cathode ray tube (CRT), a liquid crystal display (LCD), an organic LED (OLED) display, and/or an "electronic ink" display. Presentation interface 320 may include one or more display devices. In this embodiment, presentation interface 320 displays the determined Molybdenum-99 content of the sample.

Computing device 150 includes a user input interface 335 in this embodiment. User input interface 335 is coupled to processor 315 and receives input from user 325. User input interface 335 may include, for example, a keyboard, a pointing device, a mouse, a stylus, a touch sensitive panel (e.g., a touch pad or a touch screen), a gyroscope, an accelerometer, a position detector, and/or an audio user input interface. A single component, such as a touch screen, may function as both a display device of presentation interface 320 and user input interface 335. In this embodiment, computing device 150 further includes a communication interface 340 coupled to processor 315. Communication interface 340 communicates with one or more remote devices, such as first and second current measurement devices 130 and 132.

In this embodiment, computing device 150 (and more specifically, processor 315) receives the first current measurement from first current measurement device 130. Using a first conversion factor (stored, for example, in memory device 310), processor 315 converts the first current measurement into a corresponding first Molybdenum-99 content value. In this embodiment, the first Molybdenum-99 content value is calculated in millicuries (mCi). Alternatively, the first Molybdenum-99 content value may be calculated in any suitable units.

Computing device 150 (and more specifically, processor 315) also receives the second current measurement from second current measurement device 130. Using a second conversion factor (stored, for example, in memory device 310), processor 315 converts the second current measurement into a corresponding second Molybdenum-99 content value. In this embodiment, the second Molybdenum-99 content value is calculated in mCi. Alternatively, the second Molybdenum-99 content value may be calculated in any suitable units. The first and second conversion factors for calculating the first and second Molybdenum-99 content values may be obtained, for example, during a calibration process for system 100. In some embodiments, the first and second conversion factors are the same.

First and second Molybdenum-99 content values are calculated substantially simultaneously. That is, the assay process starts, and finishes, at substantially the same time for both chambers 104 and 106. In another embodiment, the assay process starts, and finishes, at exactly the same time for both chambers 104 and 106. Computing device 150 compares the first Molybdenum-99 content value with the second Molybdenum-99 content value, and generates a final Molybdenum-99 content value (e.g., to be displayed on presentation interface 320). For example, computing device 150 may determine whether first Molybdenum-99 content value and second Molybdenum-99 content value are in agreement with each other. If system 100 is operating properly, first and second Molybdenum-99 content values should generally be in agreement.

In one embodiment, computing device 150 determines first and second Molybdenum-99 content values are in agreement if a difference between first and second Molybdenum-99 content values is less than or equal to a predetermined percentage of one of the first and second Molybdenum-99 content values. In one example, if the difference (i.e., range) between first and second Molybdenum-99 content values is less than or equal to 5%, computing device 150 determines first and second Molybdenum-99 content values are in agreement. Alternatively, any predetermined percentage that enables computing device 150 to function as described herein may be used.

If the difference between first and second Molybdenum-99 content values is not less than or equal to the predetermined percentage, in this embodiment, computing device 150 generates an alert indicating that first and second Molybdenum-99 content values are not in agreement. The alert may be displayed on presentation interface 320, or may be any other audio or visual alert that notifies a user of the disagreement in Molybdenum-99 content values. In response to the alert, the user can troubleshoot operation of system 100 and attempt to determine why first and second Molybdenum-99 content values are not in agreement.

To determine the final Molybdenum-99 content value, in this embodiment, computing device 150 averages first and second Molybdenum-99 content values. The averaged value is stored in memory device 310 and may be displayed on presentation interface 320. Processor 315 may also calculate and/or display other values related to the determined Molybdenum-99 content of the sample. Further, any values calculated by processor 315 may be stored in memory device 310 and/or displayed on presentation interface 320.

Using concentric ionization chambers 104 and 106, system 100 is capable of assaying a sample for Molybdenum-99 content twice simultaneously, significantly reducing the time required to assay the sample from methods in which separate assays for Molybdenum-99 content are performed sequentially. Further, using computing device 150, system 100 automatically collects and processes data related to the Molybdenum-99 content of the sample. As radiation detection device 102 facilitates detecting the content of Molybdenum-99 using two separate chambers simultaneously, system 100 reduces handling of and exposure to the sample by technicians. Moreover, as radiation detection device 102 includes attenuating material 112, unlike some known radiation detection devices, device 102 does not require external lead shielding. However, radiation detection device 102 may include built-in shielding to protect first and second ionization chambers 104 and 106 from external, background radiation. System 100 is also specifically designed to measure a full range of Molybdenum-99 assay values, unlike existing systems for assaying Molybdenum-99 content. For example, in some embodiments, system 100 is capable of detecting from 1 mCi up to 20,000 mCi of Molybdenum-99.

Example embodiments of a system for assaying a sample are described above in detail. The system is not limited to the specific embodiments described herein, but rather, components of the system may be used independently and separately from other components described herein. For example, the radiation detection device described herein may also be used in combination with other systems and methods, and is not limited to practice with only the system as described herein.

When introducing elements of the present disclosure or the embodiment(s) thereof, the articles "a", an, "the" and "said" are intended to mean that there are one or more of the elements. The terms "comprising," "including," "containing" and "having" are intended to be inclusive and mean that there may be additional elements other than the listed elements. The use of terms indicating a particular orientation (e.g., "top", "bottom", "side", etc.) is for convenience of description and does not require any particular orientation of the item described.

As various changes could be made in the above constructions and methods without departing from the scope of the disclosure, it is intended that all matter contained in the above description and shown in the accompanying drawing(s) shall be interpreted as illustrative and not in a limiting sense.

What is claimed is:

1. A system for assaying a sample for Molybdenum-99 content, the system comprising:
   an inner ionization chamber including a well configured to receive the sample;
   an outer ionization chamber concentric with the inner ionization chamber;
   attenuating material positioned in the well;
   a computing device configured to:
      determine a first Molybdenum-99 content value of the sample based on a first current measured in the inner ionization chamber;
      determine a second Molybdenum-99 content value of the sample based on a second current measured in the outer ionization chamber; and
      determine a final Molybdenum-99 content value based on the first and second Molybdenum-99 content values.

2. The system of claim 1, wherein to determine a final Molybdenum-99 content value, the computing device is configured to average the first and second Molybdenum-99 content values.

3. The system of claim 1, wherein the computing device is further configured to:
   compare the first and second Molybdenum-99 content values to determine whether they are in agreement with one another; and
   generate an alert if the first and second Molybdenum-99 content values are not in agreement with one another.

4. The system of claim 1, wherein to compare the first and second Molybdenum-99 content values, the computing device is configured to determine whether a difference between first and second Molybdenum-99 content values is less than or equal to a predetermined percentage of one of the first and second Molybdenum-99 content values.

5. The system of claim 1, wherein the inner and outer ionization chambers are high pressure Xenon gas chambers.

6. The system of claim 1, wherein the system is configured to determine the first and second Molybdenum-99 content values simultaneously.

7. The system of claim 1, further comprising:
   a first current measurement device communicatively coupled to the computing device and configured to measure the first current in the inner ionization chamber; and
   a second current measurement device coupled to the computing device and configured to measure the second current in the outer ionization chamber.

8. The system of claim 1, wherein the inner ionization chamber is separate from the outer ionization chamber.

9. The system of claim 1, wherein the inner and outer ionization chambers are annular.

10. A method for assaying a sample for Molybdenum-99 content, the method comprising:
    placing the sample in a well of an inner ionization chamber, wherein the well includes attenuating material;
    measuring a first current in the inner ionization chamber;
    measuring a second current in an outer ionization chamber, wherein the outer ionization chamber is concentric with the inner ionization chamber;
    determining, using a computing device, a first Molybdenum-99 content value of the sample from the first measured current;
    determining, using the computing device, a second Molybdenum-99 content value of the sample from the second measured current; and
    determining, using the computing device, a final Molybdenum-99 content value based on the first and second Molybdenum-99 content values.

11. The method of claim 10, wherein determining a final Molybdenum-99 content value comprises averaging the first and second Molybdenum-99 content values.

12. The method of claim 10, further comprising:
    comparing the first and second Molybdenum-99 content values to determine whether they are in agreement with one another; and
    generating an alert if the first and second Molybdenum-99 content values are not in agreement with one another.

13. The method of claim 12, wherein comparing the first and second Molybdenum-99 content values comprises determining whether a difference between first and second Molybdenum-99 content values is less than or equal to a predetermined percentage of one of the first and second Molybdenum-99 content values.

14. The method of claim 10, wherein measuring a first current in an inner ionization chamber comprises measuring a first current in a first high pressure Xenon gas chamber, and wherein measuring a second current in an outer ionization chamber comprises measuring a second current in a second high pressure Xenon gas chamber.

15. The method of claim 10, wherein the first and second Molybdenum-99 content values of the sample are determined simultaneously.

16. The method of claim 10, wherein measuring a first current comprises measuring the first current using a first source measurement unit, and wherein measuring a second current comprises measuring the second current using a second source measurement unit.

17. A radiation detection device for assaying a sample for Molybdenum-99 content, the radiation detection device comprising:
    an inner ionization chamber including a well that receives the sample, wherein a first current is generated in the inner ionization chamber in response to an amount of Molybdenum-99 present in the sample;

an outer ionization chamber concentric with the inner ionization chamber, wherein a second current is generated in the outer ionization chamber in response to the amount of Molybdenum-99 present in the sample; and attenuating material positioned in the well of the inner ionization chamber.

18. The radiation detection device of claim 17, wherein the inner and outer ionization chambers are high pressure Xenon gas chambers.

19. The radiation detection device of claim 17, wherein the attenuating material includes at least one of tungsten and lead.

20. The radiation detection device of claim 17, wherein the inner and outer ionization chambers are annular.

\* \* \* \* \*